Figure 1:
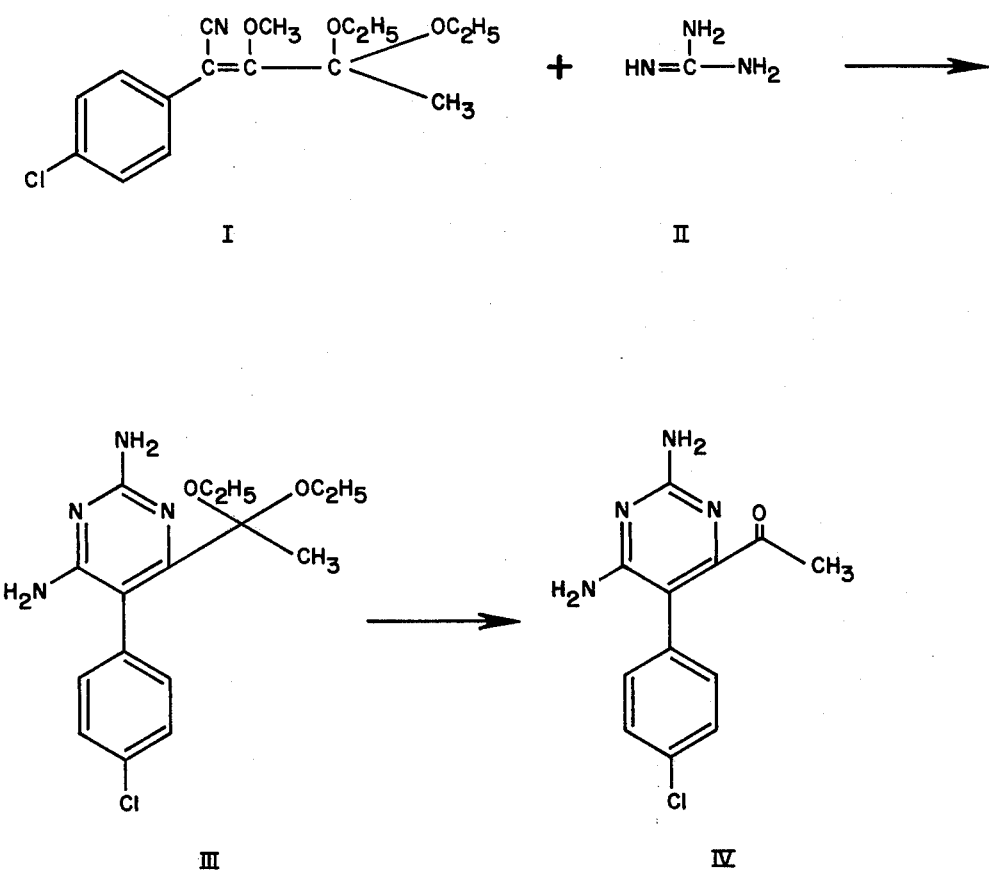

United States Patent [19]

Greenspan et al.

[11] 3,940,393
[45] Feb. 24, 1976

[54] SYNTHESIS OF 2,6-DIAMINOPYRIMIDINES
[75] Inventors: George Greenspan, Narberth; Richard W. Rees, Bryn Mawr; Peter B. Russell, Villanova, all of Pa.
[73] Assignee: American Home Products Corporation, New York, N.Y.
[22] Filed: June 21, 1974
[21] Appl. No.: 481,612

[52] U.S. Cl.. 260/256.4 N; 195/51 R; 260/256.4 C; 424/251
[51] Int. Cl.² ............. C07D 239/34; C07D 239/42

[58] Field of Search ............... 260/256.4 N, 256.4 C

*Primary Examiner*—Richard J. Gallagher
*Assistant Examiner*—James H. Turnipseed
*Attorney, Agent, or Firm*—Robert Wiser

[57] ABSTRACT

New, substituted, 2,6-diaminopyrimidines are disclosed. These compounds are useful as anti-malarial agents. The oxygenation of pyrimethamine by fungi is also disclosed.

10 Claims, 1 Drawing Figure

U.S. Patent Feb. 24, 1976 3,940,393

SYNTHESIS OF 2,6-DIAMINOPYRIMIDINES

BACKGROUND OF THE INVENTION

This invention relates to new compositions of matter classified in the art of organic chemistry as 2,6-diaminopyrimidines, and to new processes for their preparation. The new 4,5-disubstituted 2,6-diaminopyrimidines are chemically related to the known pharmaceutical, pyrimethamine, whose utility as an anti-malarial medicament is well-known.

The compounds of the instant invention are also useful as anti-malalrial agents, which activity is evidenced from the results of standard pharmacologic testing.

B. R. Baker, and J. H. Jordaan, J. Het. Chem., 4, 31, (1967) discloses the preparation of 5-(p-chlorophenyl)-2,6-diaminopyrimidine-4-carboxaldehyde. In addition to providing novel diaminopyrimidines, the present invention provides a novel process for the preparation of substances such as $(\pm)$-2,6-diamino-5-(p-chlorophenyl)-$\alpha$-methyl-4-pyrimidine methanol.

SUMMARY OF THE INVENTION

The invention sought to be patented in its composition aspect resides in the concept of a compound of the formula:

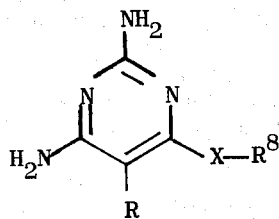

wherein R is alkoxy of from 1 to 6 carbon atoms, benzyl, phenoxy, phenyl, or phenyl substituted with one or two substituents, which may be the same or different, selected from the group of halogen, nitro, alkoxy of from 1 to 6 carbon atoms, phenoxy, and benzyl; X is

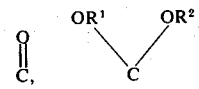

wherein $R^1$ and $R^2$ are alkyl of from 1 to 6 carbon atoms,

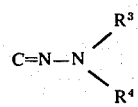

wherein $R^3$ and $R^4$ are H, alkyl of from 1 to 6 carbon atoms, or alkenyl of from 1 to 6 carbon atoms; $C=N-R^5$ wherein $R^5$ is OH, alkoxy of from 1 to 6 carbon atoms, alkanoyloxy of from 1 to 6 carbon atoms, or alkyl of from 1 to 6 carbon atoms,

wherein $R^6$ is alkyl of from 1 to 6 carbon atoms, CHB wherein B is halogen, $CHOR^7$ wherein $R^7$ is H, alkyl of from 1 to 6 carbon atoms, alkanoyl of from 1 to 6 carbon atoms, phenyl, benzyl or benzoyl; and $R^8$ is alkyl of from 1 to 6 carbon atoms, phenyl or phenyl substituted with one or two substituents, which may be the same or different, selected from the group of halogen, nitro, alkoxy of from 1 to 6 carbon atoms, phenoxy and benzyl; and the pharmacologically acceptable acid addition salts thereof.

The free base forms of the tangible embodiments of the composition aspect of the invention possess the inherent general physical properties of being off-white to white crystalline solids are substantially insoluble in water, and are generally soluble in such organic solvents as benzene, ethyl acetate, chloroform, and methanol. The acid addition salt forms of the composition aspect of the invention possess the inherent general physical properties of being off-white to white crystalline solids, are substantially insoluble in such organic solvents as benzene, ether, and chloroform and are generally soluble in water. Examination of the compounds produced according to the hereinafter described process reveals, upon infrared, proton magnetic resonance, and mass spectrographic analyses, spectral data supporting the molecular structure hereinbefore set forth.

The aforementioned physical characteristics, taken together with the nature of the starting materials and the elemental analysis of the products obtained therefrom, further confirm the molecular structure hereinbefore set forth.

The tangible embodiments of the composition aspect to the invention possess the applied use characteristic of exerting antimalarial effects in animals as evidenced by pharmacologic evaluation according to standard test procedures.

The invention sought to be patented in a first subgeneric composition aspect of the invention resides in the concept of a compound of the formula:

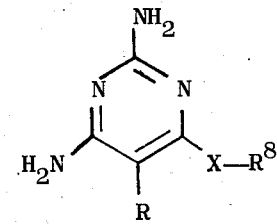

wherein R is phenyl, 3-chlorophenyl, 4-chlorophenyl, or 3,4-dichlorophenyl, X is $C(OCH_3)_2$, $C(OC_2H_5)_2$, $C=O$, $C=N-OH$, $C=N-NH_2$, $C=N-N(CH_3)_2$, CHOH, or

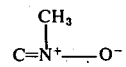

$R^8$ is alkyl of from 1 to 6 carbon atoms; and their pharmacologically acceptable acid addition salts.

The invention sought to be patented in a second subgeneric composition aspect of the invention resides in the concept of a compound of the formula:

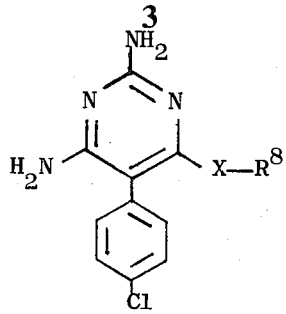

wherein X is $C(OCH_3)_2$, $C(OC_2H_5)_2$, C=O, C=N—OH, C=N—NH$_2$, C=N—N(CH$_3$)$_2$, CHOH, or

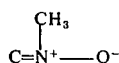

and the pharmacologically acceptable acid addition salts thereof.

The invention sought to be patented in a principal process aspect of the invention resides in the concept of a process for preparing (+)-2,6-diamino-5-(p-chlorophenyl)-α-methyl-4-pyrimidine methanol, and [2,6-diamino-5-(p-chlorophenyl)-4-pyrimidinyl]-methyl ketone which comprises contacting 2,6-diamino-5-(p-chlorophenyl)-4-ethylpyrimidine with the fungus *Pellicularia filamentosa* f. sp. *sasakii* IFO 6675.

The invention sought to be patented in a second process aspect of the invention resides in the concept of a process for preparing (+)-2,6-diamino-5-(p-chlorophenyl)-α-methyl-4-pyrimidine methanol which comprises contacting [2,6-diamino-5-(p-chlorophenyl)-4-pyrimidinyl]methyl ketone with the fungus *Corynespora cassiicola* IMI 56007.

DESCRIPTION OF THE INVENTION

For reasons of convenience, the processes of the invention are described utilizing specific embodiments of the invention, which embodiments are identified by use of Roman numerals. The use of specific embodiments to illustrate the invention is merely descriptive and is not intended to delimit the scope of the invention.

FIG. 1 depicts the preparation of the compositions of the invention by illustration of a specific embodiment thereof. Starting materials I are either known compounds or simple analogs thereof, and may be readily prepared by art-recognized methods such as those described in Bloch, Ann. Chim., 10, 583 (1965). Compound I and guanidine II, are condensed in basic medium and the 2,6-diaminopyrimidine III is produced. This condensation has been found to proceed efficiently by dissolving or suspending I in a solvent such as ethanol, isopropanol and the like, treating this mixture with a sodium or potassium lower alkoxide and reacting this basic mixture with guanidine which may conveniently be in the form of one of its acid addition salts such as its nitrate. It is the preferred method of the invention to dissolve I in ethanol, add a solution of sodium ethoxide in ethanol, add to this mixture a solution of guanidine nitrate also in ethanol and to reflux the whole mixture for several hours (two hours have been found to be sufficient). Those skilled in the art will realize that other alcohols would serve just as readily as ethanol for this reaction; thus propyl or t-butyl alcohol for example could be utilized.

It will also be obvious that other sodium alkoxides and potassium alkoxides such as potassium methoxide or potassium t-butoxide could replace sodium ethoxide as the base, and that it is not necessary to dissolve or suspend all the reaction components in the same solvent in order for the reaction to proceed.

Bases other than alkoxides and solvents other than alcohols may also be utilized, thus for example sodium hydride in dimethyl-formamide can be used. The period of heating and the temperature used are not critical aspects of the invention, but it has been observed that the reaction proceeds to near completion at a temperature of from about 65° to about 100° C. in about 2 to 4 hours.

The compound III may be isolated and purified, if desired, by standard methods known in the art, such as concentration of the reaction mixture, dilution with water and filtration of the solid thus produced.

The ketal function of III is next hydrolyzed with acid to produce IV. Alternately, III need not be isolated, and the basic reaction mixture in which III is prepared can be acidified and the hydrolysis carried out in this medium. The choice of an acid for the hydrolysis is not critical; any of the acids commonly used for ketal hydrolysis may be used. Thus for example, HCl, or H$_2$SO$_4$ may be used in either a completely, or partially aqueous medium. HCl in ethanol solution is a preferred hydrolysis medium of the invention.

It will be obvious to those skilled in the art that once IV is obtained, the ketonic carbonyl function may be reacted with a variety of reagents allowing the preparation of many derivatives. Thus the carbonyl function may be derivatized by reaction with, for example, hydrazine and substituted hydrazines, hydroxylamine, alkoxyamines, and monoalkylhydroxyl amines producing respectively, substituted and unsubstituted hydrazones, oximes, alkoxyimines, and nitrones.

Further, the foregoing carbonyl derivatives may be reduced, if desired, thus producing additional compounds.

The carbonyl function of IV may, alternately, be reduced producing the secondary alcohol V:

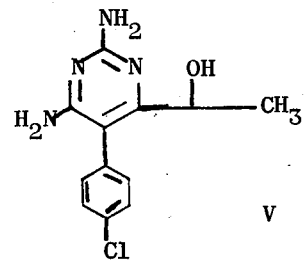

The choice of methods and necessary reagents to effect the reduction of IV to produce V is within the skill of the art; however, it is the preferred method of the instant invention to dissolve IV in a solvent such as methanol, treat the solution with sodium borohydride, reflux the mixture, for from about 1 to about 24 hours, preferably 16 hours, remove the solvent in vacuo, add water, and collect the product, V, by filtration. Other reducing agents such as diborane, and the various lithium aluminum hydride reagents in their usual solvents such as tetrahydrofuran and diethylether may also be used to effect the reduction. The choice of the reducing agent, solvent, reaction time and temperature are all within the skill of the art and are not critical aspects of the instant invention.

It will be obvious that the reaction of IV produces a molecule with an asymmetric carbon atom. The resolution of the isomers of molecules such as V is within the skill of the art, and is contemplated by the teachings of the instant invention.

Derivatives of molecules such as V may also be produced; thus, for example, the chlorine analogue may be produced by treatment with, for example, phosphorous pentachloride. An alcohol such as V may also be acylated producing esters, and dehydrated producing an olefin. Other modifications of the alcohol function will suggest themselves to those skilled in the art.

It will also be obvious, that because of the basic nature of the molecules of the instant invention, acid addition salts of these compounds can be prepared and that by the proper choice of the acid, water soluble pharmacologically acceptable salts may be produced. Examples of such acids are hydrochloric, sulfuric, fumaric and the like.

The principal process aspect of the invention comprises the microbiological oxidation of the known antimalarial medicament, pyrimethamine, [2,6-diamino-5-(p-chlorophenyl)-4-ethylpyrimidine] by the fungus *Pellicularia filamentosa* f. sp. *sasakii* IFO 6675. Other fungi of equivalent function are *Pellicularia filamentosa* f. sp. *sasakii* IFO 6258, 6297; *Pellicularia filamentosa* f. sp. *microsclerotia* CBS; *Pellicularia filamentosa* f. sp. *solani* CBS 280.36; *Pellicularia filamentosa* IFO 6476; and the like. Thus, when pyrimethamine is incubated with *Pellicularia filamentosa* f. sp. *sasakii* IFO 6675 the compounds (+)-2,6-diamino-5-(p-chlorophenyl)-α-methyl-4-pyrimidine methanol [(+)V], and [2,6-diamino-5-(p-chlorophenyl)-4-pyrimidinyl]methyl ketone (IV) are produced.

The preferred method for carrying out this microbiological oxygenation aspect of the instant invention is to contact pyrimethamine with a buffered suspension of fungal mycelial cells, for example mycelial cells of *Pellicularia filamentosa* f. sp. *sasakii* IFO 6675, for from about 1 day to about 5 days preferably from about 1.5 to about 2.5 days at about 28° C.

The temperature is not critical, but ideally is maintained between 25° C. and 30° C. The fermentation is carried out aerobically and with agitation. It will be obvious to one skilled in the art of organic chemistry that the oxygenated products IV and (+)V, may be isolated by standard procedures as for example, by extraction of the buffered solution with a water immiscible organic solvent such as methylene chloride or ethyl acetate. Drying and evaporation of the solvent followed by separation and purification of the products, for example, by chromatographic means, yields materials whose elemental analyses, infrared, proton magnetic and mass spectra are in full agreement with the structures IV and (+)V.

In the second process aspect of the instant invention, [2,6-diamino-5-(p-chlorophenyl)-4-pyrimidinyl]-methyl ketone, IV, is converted to (+)-2,6-diamino-5-(p-chlorophenyl)-α-methyl-4-pyrimidine methanol, (+)V, by the action of the fungus *Corynespora cassiicola* IMI 56007. This microbiological process is best carried out by contacting the [2,6-diamino-5-(p-chlorophenyl)-4-pyrimidinyl]methyl ketone IV with a buffered suspension of mycelial cells of the fungus *Corynespora cassiicola* IMI 56007 for from about 1 to about 5 days preferably from 2.5 to 4 days at about 28° C. The temperature is not critical, but ideally is maintained between 25° C. and 30° C. The fermentation is carried out aerobically with agitation. It will be obvious to one skilled in the art of organic chemistry that the optically active product, (+)-2,6-diamino-5-(p-chlorophenyl)-α-methyl-4-pyrimidinemethanol, may be isolated by standard procedures, as for example, by extraction of the buffered solution with a water immiscible organic solvent such as methylene chloride or ethyl acetate. Drying and evaporation of the solvent followed by purification of the product, for example by chromatographic means, yields a material whose elemental analysis, infrared, proton magnetic and mass spectra are in full agreement with the structure (+)V.

The compositions of the instant invention possess activity as anti-malarial agents, which activity is demonstrable by standard testing procedures. The compounds were tested against *Plasmodium berghei* (strain KBG 13) in mice by the procedure described by T. S. Osdene et al., J. Med. Chem. 10, 431 (1967).

Increase of the mean survival time of drug treated mice is interpreted as evidence of anti-malarial activity. Drug treated mice surviving 30 days after infection are considered to be cured. The cured-treated ratio is reported in parentheses. The following results were obtained for compositions of the present invention.

| Compound | Dose (mg/kg) | Increase in M.S.T.* in days (cured/treated) |
|---|---|---|
| [2,6-Diamino-5-(P-Chlorophenyl)-4-Pyrimidinyl]Methyl Ketone Diethyl Acetal | 40 | 3.7 |
| | 80 | 7.9 |
| | 160 | (1/5) |
| | 320 | (2/5) |
| | 640 | (5/5) |
| [2,6-Diamino-5-(P-Chlorophenyl)-4-Pyrimidinyl]Methyl Ketone | 80 | 5.9 |
| | 320 | (2/5) |
| | 640 | toxic |
| (±)-2,6-Diamino-5-(P-Chlorophenyl)-α-Methyl-4-Pyrimidinemethanol | 80 | 4.9 |
| | 160 | 9.6 |
| | 320 | 10.9 |
| | 640 | (1/5) |
| [2,6-Diamino-5-(P-Chlorophenyl)-4-Pyrimidinyl]Methyl Ketone Dimethyl Acetal | 40 | 4.5 |
| | 80 | 7.3 |
| | 160 | 9.7 |
| | 640 | (2/5) |
| (−)-2,6-Diamino-5-(P-Chlorophenyl)-α-Methyl-4-Pyrimidinemethanol, Hydrochloride, Hemihydrate | 40 | 3.9 |
| | 80 | 12.3 |
| | 160 | 13.5 |
| | 320 | (4/5) |
| | 640 | (2/5) |
| [2,6-Diamino-5-(P-Chlorophenyl)-4-Pyrimidinyl]Methyl Ketone | 40 | 3/8 |
| | 80 | 11.6 |

-continued

| Compound | Dose (mg/kg) | Increase in M.S.T.* in days (cured/treated) |
|---|---|---|
| Dimethylhydrazone | 160 | 14.8 |
|  | 320 | (2/5) |
|  | 640 | toxic |
| [2,6-Diamino-5-(P-Chlorophenyl)-4-Pyrimidinyl]Methyl Ketone Hydrazone | 160 | 8.4 |
|  | 320 | 11.4 |
|  | 640 | 14.8 |
| α-[2,6-Diamino-5-(P-Chlorophenyl)-4-Pyrimidinyl]-N,α-Dimethyl Nitrone | 160 | 3.1 |
|  | 320 | 13.3 |
|  | 640 | (2/5) |

* M.S.T. (Mean Survival Time)

It is well-known to those skilled in the art, that there are several species of plasmodia which can cause malarial infection. It will also be apparent that because of the variety of animals which can be infected, the choice of a composition and its corresponding dose necessary to treat a particular infection will vary.

The choice as well as any possible variation in the route of administration of the chosen composition will be apparent to those skilled in the art of pharmacology.

The instant compositions can be administered in a variety of dosage forms, such as tablets, capsules, suspensions or solutions.

The daily dose requirements vary with the particular compositions being employed, the severity of the symptoms being presented, and the animal being treated. The dosage also varies with the size of the animal. With large animals (about 70 kg. body weight), the daily dose is from about 10 milligrams to about 250 milligrams, and preferably from about 100 to about 150 milligrams. The prophylactic dose would be from about 15 to about 35 milligrams per day or about 125 milligrams per week.

For unit dosages, the active ingredient can be compounded into any of the usual oral dosage forms including tablets, capsules and liquid preparations such as elixirs and suspensions containing various coloring, flavoring, stabilizing and flavor masking substances. For compounding oral dosage forms the active ingredient can be diluted and various tableting materials such as starches of various types, calcium carbonate, lactose, sucrose and dicalcium phosphate to simplify the tableting and capsulating process. A minor proportion of magnesium stearate is useful as a lubricant. In all cases, of course, the proportion of the active ingredient in said composition will be sufficient to impart antimalarial activity thereto.

The best mode contemplated by the inventors of carrying out their invention is further set forth in the following nonlimiting examples:

EXAMPLE 1

[2,6-Diamino-5-(p-Chlorophenyl)-4-Pyrimidinyl]- Methyl Ketone, Diethyl Acetal

A solution of sodium (1.1 g.) in 30 ml. of ethanol together with p-chlorophenyl acetonitrile (7.6 g.) and diethoxy ethylpyruvate (9 g.) were refluxed for 4 hours. After cooling, the reaction was poured into ice, extracted with ether and the aqueous layer acidified with 17% HCl while keeping it ice cold. The acidified aqueous phase was extracted with chloroform 3 times, the combined extracts were dried and concentrated in vacuo to leave an amber oil (3.0 g.). The above oil had absorption in the IR spectrum at 3.05 (OH), 3.35 (CH), 4.52 (C≡N), 5.75 (CO), 6.15 and 6.70 (aromatic).

Without further purification the oil was dissolved in ether and treated with an excess of diazomethane, and was then left at room temperature overnight. Then the solvents were evaporated and the remaining oil (quantitative recovery), was used without further purification in the next reaction. The successful methylation of the enolic hydroxyl group was supported by the disappearance of the carbonyl absorption in the IR spectrum.

The above oil (1.5 g.) was dissolved in 10 ml. of ethanol and sodium (1.2 g.) was added in 50 ml. of ethanol containing 4.5 g. of guanidine nitrate and the whole refluxed for two hours. After concentrating in vacuo and diluting with water a precipitate can be filtered, which can be recrystallized from chloroform-methanol to yield the title compound (0.7 g.), m.p. 210°–212°.

Analysis for: $C_{16}H_{21}ClN_4O_2$; Calculated: C, 57.1; H, 6.3; N, 16.7; Cl, 10.6; Found: C, 56.4; H, 6.2; N, 16.9; Cl, 10.6.

EXAMPLE 2

[2,6-Diamino-5-(p-Chlorophenyl)-4-Pyrimidinyl]- Methyl Ketone, Hydrochloride

[2,6-Diamino-5-(p-chlorophenyl)-4-pyrimidinyl]-methyl ketone, diethyl acetal (1.0 g.) was dissolved in 50 ml. of ethanol and 5 ml. of concentrated HCl was added and the whole refluxed for 2 hours and then concentrated in vacuo to yield 700 mg. of crystalline [2,6-diamino-5-(p-chlorophenyl)-4-pyrimidinyl] methyl ketone, hydrochloride, m.p. 265° decomposition.

Analysis for: $C_{12}H_{11}ON_4Cl \times HCl$ (299.12); Calculated: C, 48.2; H, 4.0; N, 18.8; Cl, 23.7; Found: C, 48.1; H, 4.0; N, 18.8; Cl, 22.4.

EXAMPLE 3

[2,6-Diamino-5-(p-Chlorophenyl)-4-Pyrimidinyl] Methyl Ketone

A sample of [2,6-diamino-5-(p-chlorophenyl)-4-pyrimidinyl] methyl ketone, hydrochloride was dissolved in water and then precipitated with concentrated $NH_4OH$ to give the title compound, m.p. 206°–208°.

Analysis for: $C_{12}H_{11}ClN_4O$ (262.6); Calculated: C, 54.9; H, 4.2; N, 21.3; Cl, 13.5; Found: C, 54.6; H, 4.2; N, 21.6; Cl, 13.2.

EXAMPLE 4

[2,6-Diamino-5-(p-Chlorophenyl)-4-Pyrimidinyl] Methyl Ketone Dimethyl Acetal

Following the procedure of Example 1, but substituting diethoxy ethyl pyruvate by dimethoxy ethyl pyruvate [2,6-diamino-5-(p-chlorophenyl)-4-pyrimidinyl]-methyl ketone dimethyl acetal is obtained, m.p. 250°–255°.

Analysis for: $C_{14}H_{17}ClN_4O_2$ (308.77); Calculated: C, 54.5; H, 5.6; N, 18.2; Cl, 11.5; Found: C, 54.8; H, 5.7; N, 17.9; Cl, 11.4.

EXAMPLE 5

(±)-2,6-Diamono-5-(p-Chlorophenyl)-α-Methyl-4-Pyrimidine Methanol 2,6-Diamino-5-(p-chlorophenyl)-4-pyrimidinyl] methyl ketone (4.0 g.) was dissolved in 250 ml. of methanol and $NaBH_4$ (5.0 g.) was added and the whole refluxed for 16 hours. After removal of the methanol, water was added and the insoluble parts (3.5 g.) filtered. The solids were recrystallized from methanol to give (±)-2,6-diamino-5-(p-chlorophenyl)-α-methyl-4-pyrimidine methanol, m.p. 159°/187°–188°.

Analysis for: $C_{12}H_{13}ON_4Cl$ (264.5); Calculated: C, 54.5; H, 5.0; N, 21.2; Found: C, 54.1; H, 5.0; N, 21.3.

EXAMPLE 6

(±)-2,6-Diamino-5-(p-Chlorophenyl)-α-Methyl-4-Pyrimidine Methanol, Hydrochloride Dissolving (±)-2,6-diamino-5-(p-chlorophenyl)-α-methyl-4-pyrimidine methanol in a sufficient amount of ether and adding an ether solution saturated with HCl gas, gave (±)-2,6-diamino-5-(p-chlorophenyl)-α-methyl-4-pyrimidine methanol, hydrochloride, m.p. 265°–269°.

Analysis for: $C_{12}H_{13}N_4O \cdot HCl$ (301.17); Calculated: C, 47.9; H, 4.7; N, 18.6; Cl, 23.5; Found: C, 47.2; H, 4.7; N, 18.7; Cl, 23.8.

EXAMPLE 7

[2,6-Diamino-5-(p-Chlorophenyl)-4-Pyrimidinyl] Methyl Ketone Oxime

[2,6-Diamino-5-(p-chlorophenyl)-4-pyrimidinyl] methyl ketone (2.6 g.) was dissolved in 30 ml. of ethanol and hydroxylamine, hydrochloride (1.5 g.) and sodium acetate (2.5 g.) in 25 ml. of water was added and the mixture refluxed for 5 hours. After cooling a white precipitate separated; it was recrystallized from methanol to give 1.5 g. of the title product, m.p. 256°–259°.

Analysis for: $C_{12}H_{12}ClN_5O$ (277.7); Calculated: C, 51.9; H, 4.4; N, 25.2; Cl, 12.8; Found: C, 51.2; H, 4.7; N, 25.0; Cl, 12.6.

EXAMPLE 8

2,6-Diamino-5-(p-Chlorophenyl)-4-Pyrimidinyl Methyl Ketone, Hydrazone

[2,6-Diamino-5-(p-chlorophenyl)-4-pyrimidinyl] methyl ketone (1.3 g.) was dispersed in 20 ml. of absolute ethanol and 95% hydrazine (1.2 g.) (previously treated with KOH pellets overnight). The reaction was refluxed for 3 hours after which a clear solution was obtained and then cooled to room temperature. The outcoming precipitate was filtered and recrystallized from ethanol, to give crystals of 2,6-diamino-5-(p-chlorophenyl)-4-pyrimidinyl methyl ketone, hydrazone, m.p. 209°–213°.

Analysis for: $C_{12}H_{13}N_6Cl$ (276.72); Calculated: C, 52.08; H, 4.73; N, 30.37; Cl, 12.81; Found: C, 52.08; H, 4.78; N, 30.39; Cl, 12.56.

EXAMPLE 9

[2,6-Diamino-5-(p-Chlorophenyl)-4-Pyrimidinyl] Methyl Ketone, Dimethylhydrazone

[2,6-Diamino-5-(p-chlorophenyl)-4-pyrimidinyl] methyl ketone (2.6 g.) and 1,1-dimethylhydrazine (2.4 g.) was dispersed in 30 ml. of absolute ethanol. After heating to reflux, a homogeneous solution was obtained and refluxing was continued for 20 hours. After cooling a precipitate was formed which was filtered and recrystallized from ethanol-benzene to give crystals of [2,6-diamino-5-(p-chlorophenyl)-4-pyrimidinyl] methyl ketone, dimethylhydrazone, m.p. 232°–236°.

Analysis for: $C_{14}H_{17}N_6Cl$; Calculated: C, 55.17; H, 5.62; N, 25.57; Cl, 11.63; Found: C, 55.28; H, 5.80; N, 27.79; Cl, 11.62.

EXAMPLE 10

α-Methyl-α-[2,6-Diamino-5-(p-Chlorophenyl)-4-Pyrimidinyl]-N-Methylnitrone

To a solution of sodium metal (0.6 g.) in absolute alcohol (20 ml.) was added [2,6-diamino-5-(p-chlorophenyl)-4-pyrimidinyl] methyl ketone (2.0 g.) and N-methyl hydroxylamine hydrochloride (1.2 g.), and the mixture was refluxed together for 5 hours. After removal of ethanol, the residue was filtered and recrystallized from ethanol-chloroform to give α-methyl-α-[2,6-diamino-5-(p-chlorophenyl)-4-pyrimidinyl]-N-methylnitrone as a white solid, m.p. 306°–309° (decomposition).

Analysis for: $C_{13}H_{14}N_5OCl$; Calculated: C, 53.52; H, 4.84; N, 24.01; Cl, 12.15; Found: C, 53.90; H, 4.95; N, 24.21; Cl, 11.96.

EXAMPLE 11

An agar slant of *Pellicularia filamentosa* f. sp. *sasakii* IFO 6675 was washed with 5 ml. of distilled water, and one third of the resulting cell suspension was transferred to a 250 ml. Erlenmeyer flask containing 50 ml. of medium composed of

| | |
|---|---|
| Soy Peptone T (Sheffield) | 2 % |
| Dextrose | 2 % |
| Distilled water | 100 ml. |

The flask was incubated on a rotary shaker, 250 rpm., 2 inches diameter of rotation, at 28° C. for 4 days. A five ml. mycelial transfer was made to a new flask containing the original medium. Following one day of shaking at 28°, five ml. of the growth mixture was removed from the flask, and 10 mg. of 2,6-diamino-5-(p-chlorophenyl)-6-ethylpyrimidine dissolved in 0.45 ml. of dimethyl sulfoxide was added to the flask.

After the mixture had incubated for two days on the shaker, a five ml. sample was taken and adjusted to a pH between 8.0 and 9.0 with 5 N NaOH. One ml. of methyl isobutyl ketone was added and the sample-solvent combination was equilibrated.

An aliquot of the solvent extract was spotted on a TLC plate, Brinkmann F-254, and the plate was developed in a solvent mixture composed of chloroform-acetone-ethanol (8:1:1). Examination of the plate revealed two u-v quenching, Dragendorff positive products, one more polar and the other less polar than the starting material.

EXAMPLE 12

Seven agar slants of *P. filamentosa* f. sp. *sasakii* IFO 6675 were each washed with 5 ml. of distilled water, and the cell suspensions were transferred to seven one liter flasks containing 200 ml. of the medium described in Example 11. The flasks were incubated on a rotary shaker, 250 rpm., 2 inches diameter of rotation at 28° C..

After three days of growth, 12% mycelial transfers were made to a 14 liter fermentor containing eight liters of the same medium. Agitation was set at 200 rpm. and aeration at 0.25 liter of air per liter of volume per min. Following 24 hours of incubation, the mycelium was filtered off and suspended in pH 6.0 phosphate buffer. Six grams of 2,4-diamino-5-(p-chlorophenyl)-6-ethylpyrimidine dissolved in 80 ml. of dimethyl sulfoxide (DMSO) were added to the fermentor. The agitation was increased to 250 rpm. and the aeration to 0.5 liter of air per liter of volume per min.

Forty-nine hours after addition of the antimalarial substrate, the fermentation, 7.8 l, was harvested. The fermentation mixture was filtered, and the mycelium was washed with warm water. The water wash was combined with the filtrate, adjusted to pH 9.5 with 5 N NaOH, and extracted four times with six liters of ethyl acetate. The pooled solvent extracts were washed with saturated $NaHCO_3$ solution, dried over $Na_2SO_4$ and lowered in volume under reduced pressure before refrigeration at −10° C. overnight. A precipitate of 2.704 g. was formed. The solid was added to ethyl acetate, the mixture was heated, and the undissolved fraction was filtered off. The remaining solution was chilled in dry-ice-acetone to give two crops of solid material, 1.144 g., m.p. 187°–189°, and 454 mg., m.p. 190°–192°, whose $R_f$s were similar to that of the more polar product noted in Example 11.

After the two lots were combined and dissolved in ethyl acetate, the solution was treated with isopropanolic HCl to yield 1.375 g. of (−)-2,6-diamino-5-(p-chlorophenyl)-α-methyl-4-pyrimidine-methanol hydrochloride, hemihydrate, m.p. 292°–295° C.; $[\alpha]_D^{24}$ =−13.48° (C, 1.0135, ethanol). The mass spectrum (determined at 170° C/1 × $10^{-6}$ Torr., 70 electron volts) exhibited m/e = 264.

Analysis for: $C_{12}H_{13}ON_4$ . HCl . ½ $H_2O$; Calculated: C, 46.49; H, 4.87; N, 18.06; Found: C, 46.71; H, 4.69; N, 18.26.

A sample, with optical rotation of $[\alpha]_D^{26}$=−15.09 (C, 0.95 ETOH), was converted into the free base, m.p. 185°–187°, which then displayed an optical rotation of +5.29 (C, 1.03 DMF).

EXAMPLE 13

Solvent extracts obtained from several fermentations of 2,4-diamino-5-(p-chlorophenyl)-6-ethylpyrimidine with *P. filamentosa* f. sp. *sasakii* IFO 6675 were washed with saturated $NaHCO_3$ solution, lowered in volume under reduced pressure and treated with isopropanolic HCl. A total of 2,73 g. of mixed hydrochlorides was obtained.

The solid mixture was dissolved in ethanol, and the solvent solution was streaked on preparative TLC plates, Brinkmann F-254, which were developed in a chloroform-ethanol-acetone (8:1:1) mixture. The plates were run six times, and the fastest moving zone was eluted with a mixture of ethanol-chloroform (1:1). The extract was concentrated to dryness under reduced pressure and dissolved in ethyl acetate. On the addition of large volumes of ether, 179 mg. of [2,6-diamino-5-(p-chlorophenyl)-4-pyrimidinyl]methyl ketone m.p. 202°–204°, was precipitated out.

The I. R. spectrum showed $\lambda_{max}^{KBr}$ 5.9 (C=O); NMR (DMSO-$D_6$) ppm. (δ) 2.30 (s, 3), 7.38 (Q, 4). The mass spectrum exhibited m/e=262.

EXAMPLE 14

Six agar slants of *Corynespora cassiicola* IMI 56007 were each washed with 5 ml. of distilled water, and the resulting cell suspensions were transferred to six one liter flasks containing 200 ml. each of the soy peptone medium of Example 11. The flasks were shaken for 68 hours on a rotary shaker at 28° C., after which mycelial transfers, 10%, were made to a 14 liter fermentor containing eight liters of the growth medium.

Following one day of incubation, agitation 150 rpm., aeration 4 liters, temp. 28° C., the mycelium was filtered off and suspended in 8 liters of pH 6.0 phosphate buffer. The compound [2,6-diamino-5-(p-chlorophenyl)-4-pyrimidinyl]methyl ketone, 2.32 g. dissolved in 80 ml. of DMSO, was added to the fermentor, and the agitation was increased to 200 rpm. After 78 hours of incubation the mycelium was filtered off and washed with warm water. The water wash was combined with the filtrate, adjusted to pH 9.0, and extracted four times with six liters of ethyl acetate. The solvent extract was washed with saturated $NaHCO_3$ solution and dried over $Na_2SO_4$. It was next lowered in volume under reduced pressure and stored at −10° C. overnight.

A precipitate of 1.23 g. of crude product was collected, dissolved in ethyl acetate and treated with isopropanolic HCl. A first crop of 1.16 g. of the hydrochloride of (+)-2,6-diamino-5-(p-chlorophenyl)-α-methyl-4-pyrimidine-methanol was obtained, m.p. 296°–298°; $[\alpha]_D^{24}$ −25.37° (c, 1.143, ethanol); the second crop of 177 mg. had m.p. 295°–297°. NMR (DMSO-$D_6$) ppm. (δ) 1.22 (d,3), 4.42 (q,1), 7.55 (q,4). The mass spectrum exhibited m/e=264.

Analysis for: $C_{12}H_{13}ON_4$ . HCl; Calculated: C, 47.85; H, 4.69; N, 18.6; Cl, 23.54; Found: C, 47.56; H, 4.89; N, 18.47; Cl, 23.56.

EXAMPLE 15

Bis[(−)-2,6-Diamino-5-(p-Chlorophenyl)-α-Methyl-4-Pyrimidine Methanol] Dibenzoyl-d-Tartrate To (±)-2,6-diamino-5-(p-chlorophenyl)-α-methyl-4-pyrimidine methanol (52 g.) dissolved in hot methanol (5 liters) was added excess dibenzoyl-d-tartaric acid monohydrate (75 g.). The resulting solution was filtered and evaporated to smaller volume by boiling. Several crops of crystals were obtained. An extensive fractional crystallization of this material from methanol resulted in the isolation of bis[(−)-2,6-diamino-5-(p-chlorophenyl)-α-methyl-4-pyrimidine methanol]dibenzoyl-d-tartrate (234°–236° dec.) (yield 18 g.) having $[\alpha]_D^{25}$ −33.18° (c, 1.030 DMF).

Analysis for: $C_{42}H_{40}Cl_2N_8O_{10}$; Calculated: C, 56.83; H, 4.54; Cl, 7.99; N, 12.62; Found: C, 56.76; H, 4.58; Cl, 7.99; N, 12.46.

EXAMPLE 16

(−)-2,6-Diamino-5-(p-Chlorophenyl)-α-Methyl-4-Pyrimidine Methanol

To an ice-cooled magnetically stirred suspension of bis-[(−)-2,6-diamino-5-(p-chlorophenyl)-α-methyl-4-pyrimidine methanol] dibenzoyl-d-tartrate (10.4 g.) in a minimum volume of water was added dropwise excess 50% sodium hydroxide solution. After stirring a further half an hour, the suspension was collected and washed with water (yield 6.2 g.). Crystallization from methanol gave 4.8 g. of pure (−)-2,6-diamino-5-(p-chlorophenyl)-α-methyl-4-pyrimidine methanol, m.p. 204°–206°, $[\alpha]_D^{25}$ −19.32° (c, 1.014, DMF).

Analysis for: $C_{12}H_{13}ClN_4O$; Calculated: C, 54.45; H, 4.95; Cl, 13.39; N, 21.16; Found: C, 54.24; H, 4.93; Cl, 13.53; N, 21.04.

A sample of the above base $[\alpha]_D^{26}$ −18.60 (C, 1.00 DMF) was converted into its hydrochloride having a rotation of +24.86 (C, 0.99, 95% ETOH).

EXAMPLE 17

(+)-2,6-Diamino-5-(p-Chlorophenyl)-α-Methyl-4-Pyrimidine Methanol

From the above fractional crystallization of bis[(±)-2,6-diamino-5-(p-chlorophenyl)-α-methyl-4-pyrimidine methanol] dibenzoyl-d-tartrate, described in Example 15, was isolated 12.2 g. of a fraction having m.p. 210°–213° dec. and $[\alpha]_D^{25}$ −19.24° (c, 1.014, DMF).

Analysis for: $C_{42}H_{40}Cl_2N_8O_{10}$; Calculated: C, 56.83; H, 4.54; Cl, 7.99; N, 12.62; Found; C, 56.80; H, 4.47; Cl, 8.06; N, 12.44.

The base was regenerated from this salt as described for (−)-2,6-diamino-5-(p-chlorophenyl)-α-methyl-4-pyrimidine methanol, in Example 16. From 12.2 g. of the salt there was obtained 7.0 g. of crude product. Crystallization of this material from methanol gave 4.0 g. of largely racemic material having m.p. 189°–191°. Concentration of the mother liquor gave 2.4 g. of the crude dextrorotamer having m.p. 203°–206°. Recrystallization from methanol gave pure dextrorotamer, m.p. 204°–206° $[\alpha]_D^{25}$ + 16.50 (c, 1.036 DMF).

Analysis for: $C_{12}H_{13}ClN_4O$; Calculated: C, 54.45; H, 4.95; Cl, 13.39; N, 21.16; Found: C, 54.32; H, 4.71; Cl, 13.23; N, 21.02.

In preliminary experiments it was established that a good correlation existed between the optical purity and the melting point of both enantiomers of 2,6-diamino-5-(p-chlorophenyl)-α-methyl-4-pyrimidine methanol. Thus fractional crystallization of this compound from methanol as described, for example, in the isolation of the dextrorotamer, did provide reasonable evidence that complete resolution had been achieved.

The subject matter which the applicants regard as their invention is particularly pointed out and distinctly claimed as follows:

We claim:
1. A compound of the formula:

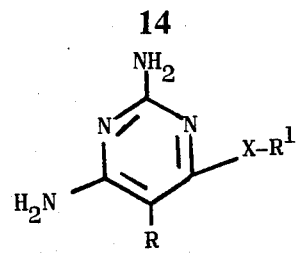

wherein R is phenyl, 3-chlorophenyl, 4-chlorophenyl, or 3,4-dichlorophenyl, X is $C(OCH_3)_2$, $C(OC_2H_5)_2$, C=O, C=N—OH, C=N—NH_2, C=N—N(CH_3)_2, CHOH, or

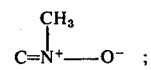

$R^1$ is alkyl of from 1 to 6 carbon atoms; and their pharmacologically acceptable acid addition salts.

2. A compound according to claim 1 of the formula:

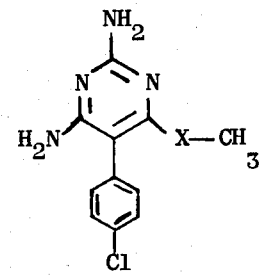

wherein X is $C(OCH_3)_2$, $C(OC_2H_5)_2$, C=O, C=N—OH, C=N—NH_2, C=N—N(CH_3)_2, CHOH, or

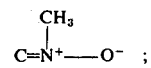

and the pharmacologically acceptable acid addition salts thereof.

3. The compound of claim 2, (±)-2,6-diamino-5-(p-chlorophenyl)-α-methyl-4-pyrimidine methanol.

4. The compound of claim 2, (+)-2,6-diamino-5-(p-chlorophenyl)-α-methyl-4-pyrimidine methanol.

5. The compound of claim 2, [2,6-diamino-5-(p-chlorophenyl)-4-pyrimidinyl]methyl ketone.

6. The compound of claim 2, [2,6-diamino-5-(p-chlorophenyl)-4-pyrimidinyl]methyl ketone, diethyl acetal.

7. The compound of claim 2, [2,6-diamino-5-(p-chlorophenyl)-4-pyrimidinyl]methyl ketone, dimethyl acetal.

8. The compound of claim 2, (−)-2,6-diamino-5-(p-chlorophenyl)-α-methyl-4-pyrimidine methanol, hydrochloride, hemihydrate.

9. The compound of claim 2, [2,6-diamino-5-(p-chlorophenyl)-4-pyrimidinyl]methyl ketone, dimethylhydrazone.

10. The compound of claim 2, [2,6-diamino-5-(p-chlorophenyl)-4-pyrimidinyl]methyl ketone oxime.

* * * * *